US005540910A

United States Patent [19]

Samain et al.

[11] Patent Number: 5,540,910
[45] Date of Patent: Jul. 30, 1996

[54] NON-MALODOROUS HAIR PERMING METHOD

[75] Inventors: Henri Samain, Bievres; Claude Dubief, Le Chesnay, both of France

[73] Assignee: L'Oreal, Paris, France

[21] Appl. No.: 50,381

[22] PCT Filed: Sep. 11, 1992

[86] PCT No.: PCT/FR92/00857

§ 371 Date: Aug. 17, 1993

§ 102(e) Date: Aug. 17, 1993

[87] PCT Pub. No.: WO93/05758

PCT Pub. Date: Apr. 1, 1993

[30] Foreign Application Priority Data

Sep. 13, 1991 [FR] France ................... 91 11325

[51] Int. Cl.$^6$ ................ A61K 7/06; A61K 7/09
[52] U.S. Cl. ........... 424/70.51; 424/70.5; 514/974
[58] Field of Search ............ 424/72, 71, 70.51, 424/70.5

[56] References Cited

U.S. PATENT DOCUMENTS

| 4,547,365 | 10/1985 | Kubo | 424/71 |
| 4,548,811 | 10/1985 | Kubo | 424/71 |
| 4,560,554 | 12/1985 | Kubo | 424/71 |
| 5,208,014 | 5/1993 | Dubief | 424/71 |

FOREIGN PATENT DOCUMENTS 8801860  3/1988  WIPO.

OTHER PUBLICATIONS

Teruo Tanimura, "Intermediate Rinse for Cold Permament Wave Setting", Patent Abstracts of Japan, vol. 8, No. 52 (C–213)(1489) 1984, JP A 58 210 006.

Hollenberg et al, "Moderne Sylingmittel–Funktion und Eigenschaften von Wellmitteln", Seifen, Öle, Fette, Wachse; vol. 117, No. 2, Feb. 1991, pp. 81–87.

Tanimura et al, "Cold wave hair treatment", Database WPIL, Section Ch, Week 8244, Derwent Publications Ltd., Class D, AN 82–93495E, JP A 57 154 116, Sep. 1982.

Primary Examiner—Sallie M. Gardner
Attorney, Agent, or Firm—Cushman Darby & Cushman L.L.P.

[57] ABSTRACT

A hair perming method including a first, reduction step using cysteamine or salt thereof, and a second, oxidizing step, is characterized in that a composition containing a monoaldehyde compound in a cosmetically acceptable carrier is applied to the hair before or after the oxidizing step, whereby the residual odor of reducing agent may be controlled effectively.

8 Claims, No Drawings

NON-MALODOROUS HAIR PERMING METHOD

The present invention relates to a new process for the permanent deformation of hair using cysteamine as the principal reducing agent, this process comprising a particular treatment to combat against a residual disagreeable odor impregnating the hair.

A known technique for effecting the permanent deformation of hair consists in carrying out, in a first stage, the opening of the disulfide bonds of keratin using a composition containing a reducing agent (reduction stage), then, after having preferably rinsed the hair, reconstituting in a second stage the said disulfide bonds by applying, on the hair under tension, an oxidizing composition (oxidation stage, also called fixation stage) so as to impart to the hair the desired definitive form. The application of the reducing composition can be carried out before or after rolling the hair on curlers.

This technique of the permanent deformation of hair permits indifferently to effect either a waving of the hair or a straightening or uncurling of the hair.

The compositions to effect the first stage of a permanent operation are generally provided in the form of lotions, creams, gels or powders to be diluted in a liquid support, and preferably contain a thiol as the reducing agent.

Among the thiols envisioned to effect the first stage of a permanent operation, cysteamine or 2-amino ethanethiol is considered particularly favorable to obtain good waving of the hair but it has been noted that the hair thus treated however develops a very disagreeable odor after a week to a month.

This unpleasant odor is more particularly perceptible when the treated hair is in the wet state or in a moist environment. Thus, the appearance of unpleasant odors is quite particularly noticeable in hot and humid climates or is even noticeable if the subject has a tendency to secrete large amounts of sebum.

From the fact of this disadvantage, cysteamine as well as its salts, even in weak amounts, is not generally employed as the reducing agent in a process for the permanent deformation of hair.

After various studies, it has now been noted, in a surprising and unexpected manner, that it is possible to prevent the appearance of unpleasant odors, due to the use of cysteamine or one of its salts by proceeding, before or after the fixation stage, to apply a composition containing a mono-aldehydic compound in a cosmetically acceptable vehicle.

The present invention thus relates to a process for the permanent deformation of hair comprising a reduction stage using a reducing composition containing cysteamine or one of its salts and an oxidation stage, this process being characterized by the fact that before or after the oxidation stage, a composition containing a mono-aldehydic compound in a cosmetically acceptable vehicle is applied to the hair so as to combat the residual disagreeable odor impregnating the hair.

There is employed as the mono-aldehydic compound in accordance with the invention, formaldehyde or an aromatic aldehyde selected from 2,4, 6-trihydroxybenzaldehyde, α-methyl-β-(p.tert.butyl phenyl) propionaldehyde, 2-methyl-4-(2,6,6-trimethyl-2(1) cyclohexene-1-yl)butanal, 2-hexyl-3-phenyl-2-propenal, 3,4-dimethoxybenzaldehyde, 2,3,4-trimethoxybenzaldehyde, 2,5-dimethoxybenzaldehyde and 4-hydroxy-3-methoxybenzaldehyde.

Preferably, the mono-aldehydic compound is used at a molar concentration between 0.15 and 1.8 moles and more preferably between 0.22 and 0.8 mole.

The cosmetically acceptable vehicle is an aqueous solution or an alcoholic or hydroalcoholic solution of a lower aliphatic alcohol such as ethanol or isopropanol.

In accordance with a preferred embodiment, according to the invention, the hair is rinsed with water prior to the application of the composition containing the mono-aldehydic compound.

The composition containing the mono-aldehydic compound can, however, contain various cosmetic ingredients such as, for example, an anionic, nonionic, amphoteric, zwitterionic or cationic surfactant, an alkalinizing or acidifying agent, a preservative, a stabilizer, a treating agent such as cations and polymers, a dye, a sunscreen agent, a thickening agent or a nacreous lustering agent.

According to the process of the invention, the composition containing the mono-aldehydic compound is applied on the hair before or after the application of the oxidizing composition for a period of time ranging from 1 to 60 minutes. After this treatment, the hair can optionally be rinsed with water, except when the mono-aldehydic compound is formaldehyde in which case it is systematically rinsed.

In accordance with a particularly preferred embodiment of the process according to the invention, the composition containing the mono-aldehydic compound is applied to the hair before the oxidation stage, the hair having previously been rinsed with water after the reduction stage.

When, in accordance with the invention, the composition containing the mon-aldehydic compound is applied after the oxidation stage, the application can be immediate or delayed in time and optionally repeated one or several times.

In accordance with the invention, the cysteamine or one of its salts, is present in the reducing composition in an amount ranging from 2 to 15 percent by weight based on the total weight of the reducing composition. The reducing composition can optionally contain a secondary reducing agent such as, for example, thioglycolic acid, glycerol thioglycolate or cysteine.

Preferably, the pH of the reducing composition is between 6 and 10 and is obtained using an alkaline agent such as, for example, ammonia, monoethanolamine, diethanolamine, triethanolamine, an ammonium or alkaline carbonate or bicarbonate, an alkaline hydroxide or with an acidifying agent such as, for example, hydrochloric acid, acetic acid, lactic acid, oxalic acid, boric acid, citric acid or phosphoric acid or even by means of a buffer such as, for example, mono and dipotassium phosphate and ammonium bicarbonate.

In accordance with a preferred embodiment of the invention, the reducing composition can also contain a surfactant of the nonionic, anionic, cationic or amphoteric type.

The reducing composition can also contain treating agents, active substances such as panthotenic acid, anti-hair loss agents, antipellicular agents, thickening agents, suspension agents, sequesterants, opacifiers, dyes, sunscreen filters as well as perfumes and preservatives and optionally other reducing agents.

The oxidizing composition is of the type currently employed and contains as the oxidizing agent, $H_2O_2$, an alkaline bromate, a persalt, a polythionate or a mixture of an alkaline bromate and a persalt. The concentration of $H_2O_2$ can vary from 1 to 20 volumes and preferably from 1 to 10 volumes; the concentration of alkaline bromate from 2 to 12 percent and that of the persalt from 0.1 to 15 percent by weight relative to the total weight of the oxidizing composition. The pH of the oxidizing composition is generally between 2 and 8, but preferably between 3 and 6.

The following non-limiting examples are given as an illustration of the process of the present invention for the permanent deformation of hair.

EXAMPLES

Example 1

On moistened hair, previously rolled up on rollers having a diameter of 14 mm, the following reducing composition is applied:
Composition (A)

| | |
|---|---|
| Cysteamine hydrochloride | 11.3 g |
| Oleocetyldimethylhydroxyethyl ammonium chloride, in aqueous solution at 30% of active material | 0.39 g (active material) |
| Ammonia, sufficient for pH = 8.5 | |
| water, sufficient amount for | 100 g |

After letting composition (A) act on the hair for 15 minutes, the hair is rinsed with running water and the following composition (B) is applied to the hair:
Composition (B)

| | |
|---|---|
| Formaldehyde | 0.2 g |
| Water, sufficient amount for | 100 g |

Composition (B) is permitted to act on the hair for 15 minutes at which time the hair is again rinsed with running water before applying the following oxidizing composition (C):
Composition (C)

| | |
|---|---|
| $H_2O_2$ in aqueous solution at 200 volumes | 4.8 g |
| Citric acid, sufficient for pH = 3 | |
| Water, sufficient amount for | 100 g |

After having let the oxidizing composition (C) act on the hair for 5 minutes, the hair is rinsed with water. The rollers are then removed and the hair is dried.

The formation of unpleasant odors over time, even after moistening the hair, is not observed.

As a comparison, the same process is carried out but omitting the treatment using composition (B). After a certain period of time it is noted that the hair gives off an unpleasant odor.

COMPARATIVE STUDIES

A. Treatment before the oxidation stage:

Ten hair samples, each weighing about 2.5 g are treated using a shampoo and then rinsed. On each of the samples the following reducing composition is applied:

| | |
|---|---|
| Cysteamine hydrochloride | 9.6 g |
| Tegobetaine | 1 g |
| Ammonia, 20% in water, sufficient for pH = 8.5 | |
| Demineralized water, sufficient amount for | 100 g |

After having let this reducing composition act on the hair samples for 15 minutes, all ten of the hair samples are rinsed with water.

One of the samples is reserved as a control and the remaining nine hair samples are treated, respectively, by the following 1 to 9 treating compositions:

| Composition 1 | |
|---|---|
| 2,4,6-trihydroxybenzaldehyde | 7.7 g |
| Ethyl alcohol | 50 g |
| Demineralized water, sufficient for | 100 g |
| Composition 2 | |
| α-methyl-β-(p.tert.butylphenyl) propionaldehyde, sold under the trade name "LILIAL" by Givaudan | 8 g |
| Ethyl alcohol, sufficient for | 100 g |
| Composition 3 | |
| 2-methyl-4-(2,6,6-trimethyl-2(1)-cyclohexene-1-yl) butanal, sold under the trade name "CETONAL", by Givaudan | 9.1 g |
| Ethyl alcohol, sufficient for | 100 g |
| Composition 4 | |
| 3,4-dimethoxybenzaldehyde | 6.2 g |
| Ethyl alcohol, sufficient for | 50 g |
| Demineralized water, sufficient for | 100 g |
| Composition 5 | |
| 2,3,4-trimethoxybenzaldehyde | 9.8 g |
| Ethyl alcohol, sufficient for | 100 g |
| Composition 6 | |
| 2,5-dimethoxybenzaldehyde | 8.3 g |
| Ethyl alcohol, sufficient for | 100 g |
| Composition 7 | |
| 2-hexyl-3-phenyl-2-propenal, sold under the trade name "HEXYL CINNAMIC ALDEHYDE", by Givaudan | 10.8 g |
| Ethyl alcohol, sufficient for | 100 g |
| Composition 8 | |
| Formaldehyde, 30% in water | 3 g |
| Demineralized water, sufficient for | 100 g |
| Composition 9 | |
| 4-hydroxy-3-methoxybenzaldehyde | 7.6 g |
| Ammonia, 20% in water, sufficient for pH = 8.5 | |
| Demineralized water, sufficient for | 100 g |

After having let these composition act on their respective hair samples for about 15 minutes the hair samples are thoroughly rinsed and there is applied to the nine hair samples thus treated and on the control sample an oxidizing composition constituted of:

| | |
|---|---|
| $H_2O_2$, at 8 volumes | 100 g |
| Citric acid, sufficient from pH = 3 | |

After a contact time of 5 minutes, the ten hair samples are rinsed with water.

After drying, the hair samples are suspended in separate compartments for 4 days.

After the second day, the hair samples are shampooed, washed with water and dried.

On the fourth day, the hair samples are sprayed with water and submitted to a panel of 4 persons, so as to determine if they emit any residual odor. The intensity of the odor is ranked according to the following scale:

| | |
|---|---|
| 0 | no odor |
| 1 | very weak odor |
| 2 | weak odor |
| 3 | perceptible odor |
| 4 | pronounced odor |
| 5 | strong odor |
| 6 | very strong odor. |

The results obtained are set forth in the following table:

| ♦Sample No. | Treatment Composition | Average rating of perceived odor |
|---|---|---|
| 1 (Control) | — | 5.75 |
| 2 | 1 | 1 |
| 3 | 2 | 1 |
| 4 | 3 | 1.5 |
| 5 | 4 | 1 |
| 6 | 5 | 1 |
| 7 | 6 | 3 |
| 8 | 7 | 1.25 |
| 9 | 8 | 2.25 |
| 10 | 9 | 2 |

As can be seen, the treatment of the hair samples between the reduction stage and the oxidation stage, using a composition containing a mono-aldehydic compound, very strongly reduces the presence of residual odors. Only composition (6), applied to hair sample (7) and containing 2,5-dimethoxybenzaldehyde gives a result perceptibly inferior to the other compositions.

B. Treatment after the oxidation stage

In accordance with the same operating procedures described above in part A, nine hair samples are treated using the following reducing composition:

| | |
|---|---|
| Cysteamine hydrochloride | 10 g |
| Glycerol thioglycolate | 3.1 g |
| Tegobetaine | 1 g |
| Ammonia, 20% in water, sufficient for pH = 7.5 | |
| Demineralized water, sufficient for | 100 g |

After having let this reducing composition remain in contact with the hair samples for 15 minutes, the hair samples are rinsed with water and the following oxidizing composition is applied to the rinsed hair samples:

| | |
|---|---|
| H$_2$O$_2$ at 8 volumes | 100 g |
| Citric acid, sufficient for pH = 3 | |

After having let the oxidizing composition react on the hair samples for 5 minutes, 8 of these samples (1 being reserved as a control) are treated, respectively, with the following treating compositions Nos. 10 to 17.

| | |
|---|---|
| Composition 10 | |
| 2,4,6-trihydroxybenzaldehyde | 6 g |
| Ethyl alcohol | 50 g |
| Demineralized water, sufficient for | 100 g |
| Composition 11 | |
| α-methyl-β-(p-tert.butylphenyl) propionaldehyde | 5 g |
| Ethyl alcohol, sufficient for | 100 g |
| Composition 12 | |
| 2-methyl-4-(2,6,6-trimethyl-2(1)- cyclohexene-1-yl) butanal | 5.2 g |
| Ethyl alcohol, sufficient for | 100 g |
| Composition 13 | |
| 3,4-dimethoxybenzaldehyde | 4.2 g |
| Ethyl alcohol, sufficient for | 50 g |
| Demineralized water, sufficient for | 100 g |
| Composition 14 | |
| 2,3,4-trimethoxybenzaldehyde | 4.85 g |
| Ethyl alcohol, sufficient for | 100 g |
| Composition 15 | |
| 2,2-dimethoxybenzaldehyde | 5.8 g |
| Ethyl alcohol, sufficient for | 100 g |
| Composition 16 | |
| 2-hexyl-3-phenyl-2-propenal | 8.8 g |
| Ethyl alcohol, sufficient for | 100 g |
| Composition 17 | |
| 4-hydroxy-3-methoxybenzaldehyde | 6.8 g |
| Ammonia, 20% in water, sufficient for pH = 8.5 | |
| Demineralized water, sufficient for | 100 g |

The hair samples, including the control sample, are submitted after 4 days to a panel of 4 persons so as to determine if they give off residual odors in accordance with the same scale as that given above in part (A).

The results obtained are set forth in the following table:

| Sample No. | Treatment composition | Average rating of perceived odor |
|---|---|---|
| 1 (Control) | — | 5.75 |
| 2 | 10 | 2.25 |
| 3 | 11 | 2 |
| 4 | 12 | 2 |
| 5 | 13 | 1.75 |
| 6 | 14 | 2 |
| 7 | 15 | 3 |
| 8 | 16 | 2.25 |
| 9 | 17 | 1.75 |

The results obtained show that with respect to the control sample, the reduction of the residual odor is quite significant. On comparing the results of the treatment studies, before or after the oxidation stage, it can be noted in a surprising manner, that a more perceptible reduction of residual odors is obtained when the composition containing the mono-aldehydic compound is applied before the oxidizing composition.

We claim:

1. A process for the permanent deformation of hair, comprising the steps of:

(1) applying to said hair a reducing composition in an amount and for a time sufficient to reduce the disulfide bonds of keratin, said composition containing, as a reducing agent, cysteamine or a salt thereof, and (2) then applying to said hair, prior or subsequent to the application of an oxidizing composition to reform said disulfide bonds, a composition containing, in a cosmetically acceptable vehicle, an effective amount of a mono-aldehydic compound selected from the group consisting of formaldehyde, α-methyl-β-(p-tert-butylphenyl) propionaldehyde, 2-methyl-4-(2,6,6-trimethyl-2(1)cyclohexene-1-yl) butanal and 2-hexyl-3-phenyl-2 propenal, said composition containing said mono-aldehydic compound being applied to said hair in an amount and for a time sufficient to prevent the unpleasant odors of the reducing agent.

2. Process according to claim 1, wherein said mono-aldehydic compound is present in a molar concentration between 0.15 and 1.8 mole.

3. Process according to claim 1, wherein said cosmetically acceptable vehicle is an aqueous solution or an alcoholic or hydroalcoholic solution of a lower aliphatic alcohol.

4. Process according to claim 1, wherein said composition containing the mono-aldehydic compound further contains at least one cosmetic ingredient selected from the group consisting of an anionic, nonionic or amphoteric or zwitterionic or cationic surfactant, an alkalinizing or acidifying agent, a preservative agent, a stabilizer, a treating agent, a dye, a solar filter, a thickening agent and a nacreous lustering agent.

5. Process according to claim 1, wherein said hair is rinsed with water prior to the application of the composition containing the mono-aldehydic compound.

6. Process according to claim 1, wherein said composition containing the mono-aldehydic compound is applied on the hair during a time of 1 to 60 minutes.

7. Process according to claim 1, wherein said composition containing the mono-aldehydic compound is applied on the hair before the oxidation stage, the hair having previously been rinsed with water after the reduction stage.

8. Process according to claim 1 wherein an aqueous composition of formaldehyde is applied to the hair and then the hair is rinsed with water.

* * * * *